(12) United States Patent
Sugaya et al.

(10) Patent No.: US 6,642,058 B2
(45) Date of Patent: Nov. 4, 2003

(54) ANALYSIS METHOD USING DRY CHEMICAL ANALYSIS ELEMENT

(75) Inventors: Fumio Sugaya, Kanagawa-ken (JP);
Yoichi Endo, Kanagawa-ken (JP);
Nobuaki Tokiwa, Kanagawa-ken (JP);
Akihiro Komatsu, Kanagawa-ken (JP);
Yoshihiro Seto, Kanagawa-ken (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 235 days.

(21) Appl. No.: 09/853,751

(22) Filed: May 14, 2001

(65) Prior Publication Data
US 2001/0041367 A1 Nov. 15, 2001

(30) Foreign Application Priority Data
May 12, 2000 (JP) .............................. 2000/140337

(51) Int. Cl.[7] .............................................. G01N 33/48
(52) U.S. Cl. .................. 436/169; 436/164; 422/58; 422/61
(58) Field of Search .............................. 422/56, 58, 61; 436/164, 169

(56) References Cited

U.S. PATENT DOCUMENTS

| 4,823,169 | A | | 4/1989 | Ogura | ........................ 356/446 |
| 4,959,796 | A | * | 9/1990 | Hidaka et al. | ................. 702/19 |

OTHER PUBLICATIONS

Abstract, May 12, 1995, JP 7120477 A.

* cited by examiner

Primary Examiner—Lyle A. Alexander
(74) Attorney, Agent, or Firm—Sughrue Mion, PLLC

(57) ABSTRACT

An analysis method using a dry chemical analysis element accurately measures change in optical density indicating the composition of a liquid sample without requiring accurate control of the amount and position of the liquid sample dripped on the dry chemical analysis element. A one-dimensional or two-dimensional optical reading apparatus measures one-dimensional or two-dimensional distribution of degree of color reaction for a reacted portion of the dry chemical analysis element. Concurrently, the one-dimensional or two-dimensional optical reading apparatus measures a length or a spread area of the reacted portion. Physical density or activity of a target component contained in the liquid sample is determined based on an integrated value of the degree of the color reaction and the measured length or the spread area of the reacted portion.

4 Claims, 5 Drawing Sheets

F I G. 3A
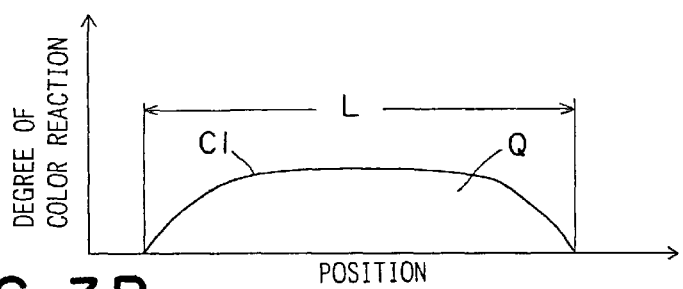
F I G. 3B
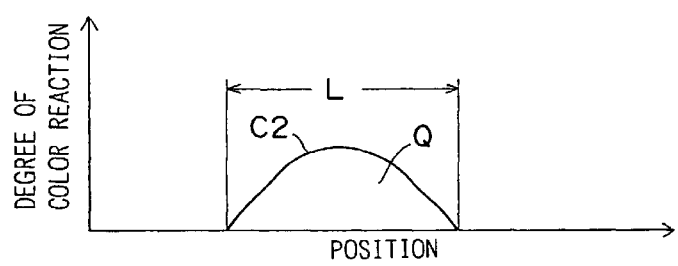
F I G. 4
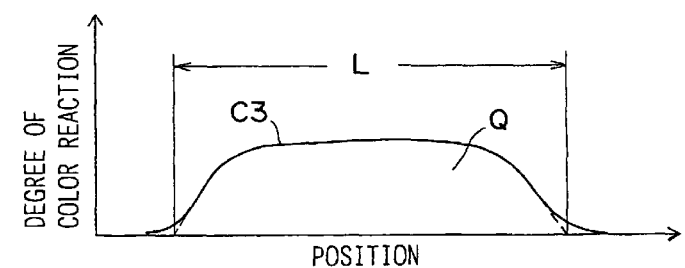
F I G. 5
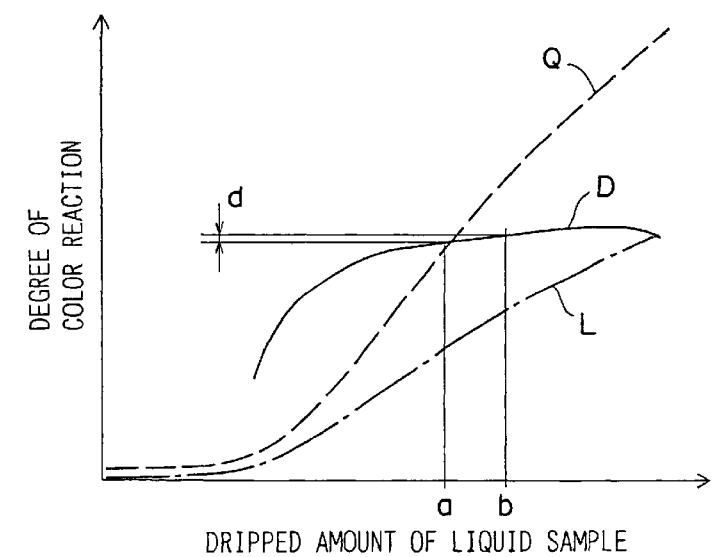

ANALYSIS METHOD USING DRY CHEMICAL ANALYSIS ELEMENT

BACKGROUND OF THE INVENTION

1. Field of the Invention

This invention relates to an analysis method for determining physical density or activity of a specific biochemical component contained in a liquid sample (e.g., blood or urine) dripped on a dry chemical analysis element having a reagent layer by measuring change in optical density of a reacted portion on the dry chemical analysis element where color reaction has occurred, wherein the color reaction is chemical reaction, biochemical reaction or immunoreaction between the reagent layer and the specific biochemical component.

2. Description of the Related Art

Recently, there has been put into practice a dry chemical analysis element of an integrated multi-layered type, which is used to determine physical density or activity of a specific chemical component contained in a liquid sample dripped thereon, or to determine physical density of solid component contained in the liquid sample dripped thereon. Further, analysis elements of similar functions, e.g., filter-paper type elements and applications thereof (including both single layer types and multi-layered types) have also been developed and partly put into practice.

When quantitatively analyzing the chemical components or the like contained in the liquid sample using a dry chemical analysis element, the liquid sample is dripped onto the chemical analysis element (onto a spreading layer when the element is provided with the spreading layer or directly onto the reagent layer when the element is not provided with the spreading layer). The dry chemical analysis element is thereafter held at a constant temperature for a predetermined time in an incubator, so that coloring reaction (pigment-generating reaction or color-changing reaction of the reagent) is promoted on the dry chemical analysis element. After the coloring reaction, change in the optical density of the reacted portion is optically measured. That is, measurement light including a wavelength, which is pre-selected according to the combination of the target chemical component and the reagent contained in the reagent layer, is projected onto the dry chemical analysis element to measure the change in the optical density of the reacted portion on the reagent layer. Then the physical density or the activity of the chemical component is determined based on of the measured optical density referring to a predetermined calibration curve depicting the relationship between the physical density or the activity of the chemical component and the change in the optical density.

The dry chemical analysis element of the integrated multi-layered type generally comprises a substrate of an organic polymer and at least one reagent layer formed on the substrate. Preferably, the dry chemical analysis component additionally comprises a spreading layer superposed on the reagent layer. The dry chemical analysis element of the integrated multi-layered type is generally in the form of a film chip of a predetermined shape such as a square or a rectangle. The film chip may be provided with a frame of an organic polymer for facilitating automated handling of the dry chemical analysis element. Also, there has been proposed an analysis technique of using the film chip by itself without use of the frame.

The optical density of the reacted portion can be measured by extracting light of a certain wavelength from the measurement light emitted by a light source using an interference filter or the like, guiding the light of a certain wavelength through optical fibers or the like, focusing the guided light onto a spot on the dry chemical analysis element using a lens, and measuring reflected light from the spot using a photo-detector mounted in a photometric head. Examples of such a technique for measuring the optical density are disclosed in, for example, Japanese Patent Publication No. 5(1993)-72976 and Japanese Unexamined Patent Publication No. 7(1995)-120477.

However, there has been a problem with the above technique for measuring the optical density that accuracy of measurement may be degraded because of non-uniformity in the amount of the liquid sample dripped on the element or because of difference between an accurate sample-dripped position and a measured position. For this reason, a relatively large amount of the liquid sample has been required to maintain the accuracy of measurement at a reasonable level.

In addition, when the measurement light is focused onto an area having no liquid sample spread thereon or onto a boundary area where only an insufficient amount of the liquid sample has been spread, a large error may be included in the measured optical density because strong reflection may occur on such an area despite little or no liquid sample being spread thereon. Thus, it is preferable to focus the measurement light not onto such an area, but onto an area where a sufficient amount of the liquid sample has been spread.

In this respect, the dry chemical analysis element is usually provided with the spreading layer superposed on the reagent layer, so that the liquid sample dripped substantially onto the center of the element may spread isotropically to provide an area capable of effective color reaction which is sufficiently larger than the beam spot of the measurement light. The measurement light is required to have a beam spot of 4–6 mm in diameter so that a sufficiently large amount of the reflected light is obtained to maintain the accuracy of measurement at a reasonable level. The amount of the liquid sample required to spread beyond such a beam spot is about 10 $\mu$l. Even if the required amount of the liquid sample is dripped on the spreading layer, about 50% of the liquid sample may constitute a non-uniform component which makes the reflection amount due to the color reaction non-uniform, instead of spreading uniformly over the entire spreading layer. Influence of such spreading characteristics upon the measuring accuracy may be reduced by accurately regulating the dripping amount of the liquid sample. However, the dripping amount of the liquid sample must be regulated by controlling injection and aspiration of the liquid sample with high accuracy, which is extremely difficult in practice.

In practical implementation, there may be a slight difference between the accurate sample-dripped position (i.e., the position where the most active color reaction occurs) and the measured position. When the difference becomes large, a large error may be included in the measured optical density because the measured optical density may reflect the state at the position with an insufficient amount of the liquid sample where only a low degree of the color reaction has occurred. To avoid such an error, the liquid sample is required to be spread over a relatively large area so that the measured position falls within the covered area. In this respect, a relatively large amount of the liquid sample must be collected, which is burdensome for a weak patient (e.g., a patient in a serious state, an old patient or a child) and which may be impossible for a subject such as a small animal.

Describing in detail referring to figures, shown in FIG. 7A is a sectional view of a dry chemical analysis element 1 in a slide-like form including a film chip 2 held by a frame 3. The frame 3 has a circular aperture at the center thereof. The film chip 2 includes a substrate, at least one reagent layer formed on the substrate, and a spreading layer superposed on the reagent layer. FIG. 7B is a plane view of the dry chemical analysis element 1 of FIG. 7A, provided with a sufficient amount of the liquid sample dripped thereon. FIG. 7C is another plane view of the same dry chemical analysis element 1, but provided with only an insufficient amount of the liquid sample dripped thereon. In FIGS. 7B and 7C, the cross-hatched portions P1 and P2 indicate the reacted portions where the color reaction has occurred.

FIG. 8 is a schematic view showing a possible structure of an existing photometric head 50 for measuring the optical density of the reacted portion on the dry chemical analysis element 1. The photometric head 50 in FIG. 8 includes an optical fiber 51 for guiding the measurement light of a suitable wavelength onto a measuring surface of the film chip 2 so that the right angle of incidence can be attained, a collective lens 52 for collecting the light emitted from the optical fiber 51, and a pair of photo-detectors 53 for detecting the light reflected by the measuring surface of the film chip 2. The measurement light from the photometric head 50 is focused onto the reacted portion as a beam having a beam spot 54 of a predetermined radius. The optical density is calculated from the intensity of the reflected light detected by the photo-detectors 53. Then, the physical density or the activity of the target chemical component is determined referring to a predetermined calibration curve representing the relationship between the physical density or the activity of the chemical component and the change in the optical density.

Shown in FIG. 9 are distribution curves for degree of the color reaction on the dry chemical analysis element 1 and the sensitivity of the photometric head 50. Herein, the term "degree of the color reaction" means the same as the term "the change in the optical density." The curve C1 represents the distribution of the degree of the color reaction for the reacted portion P1 in FIG. 7B on the dry chemical analysis element 1 provided with a sufficient amount of the liquid sample. The curve C2 represents the distribution of the degree of the color reaction for the reacted portion P2 in FIG. 7C on the dry chemical analysis element 1 provided with an insufficient amount of the liquid sample. Each curve indicates that substantially constant degree of the color reaction is attained in the central area, and that the degree of the color reaction gradually decreases in the boundary area. The curve R represents the distribution of the sensitivity of the photometric head 50. The curve R indicates that the sensitivity is high at the center of the beam spot 54 but sharply decreases near the boundary of the beam spot 54.

When projecting the measurement light onto the dry chemical analysis element 1 on which sufficient degree of the color reaction has occurred over the area larger than the beam spot 54, as indicated by the curve C1, an effective result can be obtained as the intensity of the reflected light detected by the photo-detectors 53 accurately reflects the degree of the color reaction throughout the measured area. On the other hand, the result is not effective when the measurement light is projected onto the dry chemical analysis element 1 on which sufficient degree of the color reaction has occurred only within an area smaller than the beam spot 54, as indicated by the curve C2, as the reflected light detected by the photo-detectors 53 includes a light component reflected by the boundary area and/or the area outside the boundary area where only insufficient degree of the color reaction or no color reaction has occurred. The boundary area and/or the area outside the boundary area may reflect the light projected thereon by a larger reflectance than the area where the sufficient color reaction has occurred. Because of such an intense reflected light component which does not reflect the degree of the color reaction, a large error may be included in the calculated degree of the color reaction, making an effective quantitative analysis impossible. Thus, the liquid sample is always required to be spread over a relatively large area to realize the distribution of the degree of the color reaction as indicated by the curve C1. Accordingly, a relatively large amount of the liquid sample must be dripped on the dry chemical analysis element 1. In addition, the sample-dripped position must be accurately controlled to avoid a large separation between the sample-dripped position and the actually measured position.

FIG. 10 is a diagram showing the relationship between the dripped amount of the liquid sample and the degree of the color reaction. As the dripped amount of the liquid sample increases, the area over which the liquid sample is spread becomes larger. Concurrently, the amount of the liquid sample per unit area also increases at each point within the area over which the liquid sample has already been spread, resulting in a higher degree of the color reaction at each point. That is, even if the liquid sample is spread over an area sufficiently larger than the spot 54, the measured degree D of the color reaction may include an error d due to the difference between the dripped amount of the liquid sample, b-a. To minimize the error d, the liquid sample must be dripped accurately by a constant amount.

SUMMARY OF THE INVENTION

An object of the present invention is to provide an analysis method using a dry chemical analysis element with which the change in the optical density indicating the composition of a liquid sample can be measured accurately without accurate control of the amount and position of the liquid sample dripped on the dry chemical analysis element.

According to a first aspect of the present invention, there is an analysis method using a dry chemical analysis element comprising the steps of: dripping a liquid sample onto the dry chemical analysis element including a reagent layer, measuring change in optical density of a reacted portion on the dry chemical analysis element where color reaction between the liquid sample and the reagent layer has occurred, and determining physical density or activity of a specific biochemical component contained in the liquid sample; wherein the step of measuring the change in the optical density comprises the steps of: measuring one-dimensional distribution of the change in the optical density along a straight line crossing a central portion of the reacted portion by causing a one-dimensional optical reading apparatus to scan the straight line, and measuring a length of the reacted portion along the straight line crossing the central portion of the reacted portion using the one-dimensional optical reading apparatus; and wherein the physical density or the activity is determined based on an integrated value of the change in the optical density and the measured length of the reacted portion.

According to a second aspect of the present invention, there is an analysis method using a dry chemical analysis element comprising the steps of: dripping a liquid sample onto the dry chemical analysis element including a reagent layer, measuring change in optical density of a reacted portion on the dry chemical analysis element where color reaction between the liquid sample and the reagent layer has occurred, and determining physical density or activity of a specific biochemical component contained in the liquid sample; wherein the step of measuring the change in the optical density comprises the steps of: measuring one-dimensional distribution of the change in the optical density along a straight line crossing a central portion of the reacted portion by causing a one-dimensional optical reading apparatus to scan the straight line, calculating two boundary positions of the reacted portion based on slopes of the obtained one-dimensional distribution of the change in the optical density, and defining distance between the two boundary positions as a length of the reacted portion; and wherein the physical density or the activity is determined based on an integrated value of the change in the optical density and the defined length of the reacted portion.

According to a third aspect of the present invention, there is an analysis method using a dry chemical analysis element comprising the steps of: dripping a liquid sample onto the dry chemical analysis element including a reagent layer, measuring change in optical density of a reacted portion on the dry chemical analysis element where color reaction between the liquid sample and the reagent layer has occurred, and determining physical density or activity of a specific biochemical component contained in the liquid sample; wherein the step of measuring the change in the optical density comprises the steps of: measuring two-dimensional distribution of the change in the optical density over an entire spread area of the reacted portion by causing a two-dimensional optical reading apparatus to scan the entire spread area, and measuring the spread area of the reacted portion using the two-dimensional optical reading apparatus; and wherein the physical density or the activity is determined based on an integrated value of the change in the optical density and the measured spread area.

According to a fourth aspect of the present invention, there is an analysis method using a dry chemical analysis element comprising the steps of: dripping a liquid sample onto the dry chemical analysis element including a reagent layer, measuring change in optical density of a reacted portion on the dry chemical analysis element where color reaction between the liquid sample and the reagent layer has occurred, and determining physical density or activity of a specific biochemical component contained in the liquid sample; wherein the step of measuring the change in the optical density comprises the steps of: measuring two-dimensional distribution of the change in the optical density over an entire spread area of the reacted portion by causing a two-dimensional optical reading apparatus to scan the entire spread area, calculating a boundary of the reacted portion based on slopes of the measured two-dimensional distribution of the change in the optical density, and defining an area within the calculated boundary as the spread area of the reacted portion; and wherein the physical density or the activity is determined based on an integrated value of the change in the optical density and the measured spread areaof the reacted portion.

According to the above analysis methods of the present invention, the change in the optical density can be measured with a stable accuracy even if the center of the straight line or the spread area scanned by the one-dimensional or two-dimensional optical reading apparatus does not match accurately with the exact center of the reacted portion. Thus, sufficiently accurate measurement can be carried out regardless of the fluctuation of the amount and/or position of the liquid sample dripped on the dry chemical analysis element. In addition, the measurement can be carried out with a sufficient accuracy requiring only a small amount of the liquid sample. Accordingly, the entire process of analysis is simplified to provide an easy analysis method at a low cost.

BRIEF DESCRIPTION OF THE DRAWINGS

FIGS. 3A and 3B are examples of measured distributions of degree of color reaction (i.e., change in optical density), FIG. 4 illustrates a method of defining a length of a reacted portion based on a distribution of the degree of the color reaction, FIG. 5 is a diagram showing a relationship between the dripped amount of the liquid sample and the average degree of the color reaction, together with an integrated value of the degree of the color reaction and the length of the reacted portion.

DESCRIPTION OF THE PREFERRED EMBODIMENT

Figure 1:
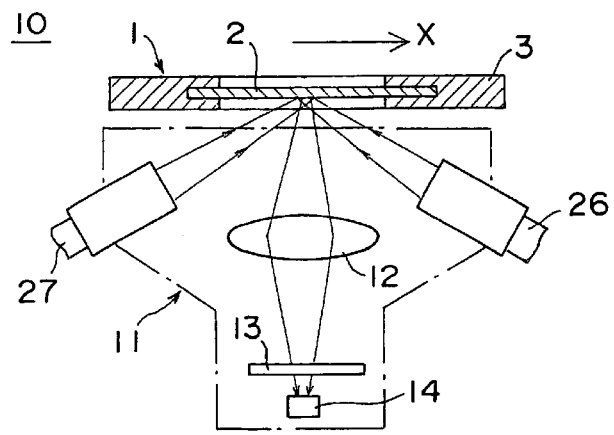
FIG. 1 is a schematic view showing the structure of a photometric head of a one-dimensional optical reading apparatus used in implementing the first and second embodiments of the present invention.
Figure 2:
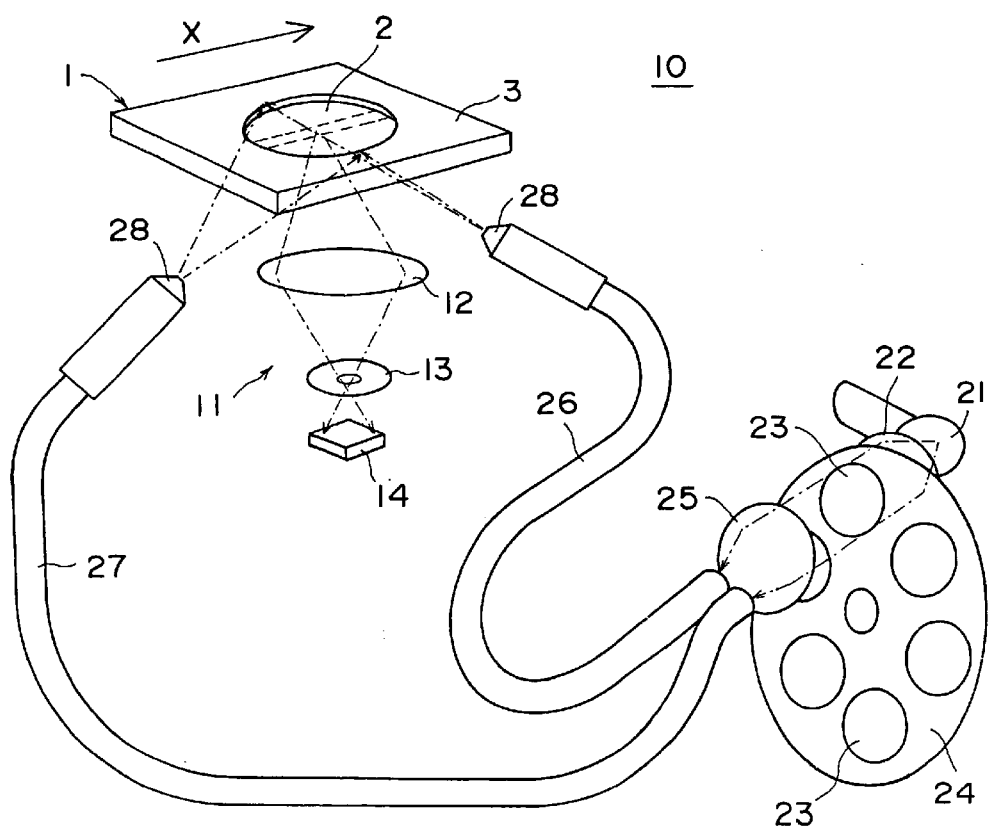
FIG. 2 is a schematic perspective view of the one-dimensional optical reading apparatus.

Now, embodiments of the present invention will be described with reference to accompanying drawings. FIG. 1 is a schematic view showing the structure of a photometric head used in implementing an analysis method according to the first and second embodiments of the present invention, and FIG. 2 is a schematic perspective view thereof.

Figure 7A:
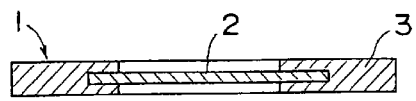
FIG. 7A is a sectional view of a dry chemical analysis element.

As shown in FIG. 7A, a dry chemical analysis element 1 used in the embodiments herein is such a one in a slide-like form including a square or rectangular film chip 2 held by a frame 3. Specifically, the film chip 2 includes a plastic sheet (e.g., a sheet of an organic polymer such as polyethylene telephthalate (PET) or polystyrene) as a light transmitting substrate, at least one reagent layer applied or adhered onto the substrate, and a spreading layer superposed on the reagent layer by a laminating method etc. The frame 3 is a frame of an organic polymer provided for facilitating automated handling of the dry chemical analysis element 1.

Each reagent layer is a layer of a hydrophilic polymer binder or a porous layer, containing a reagent which reacts selectively with the target component of the analysis and a reagent required for color reaction. The spreading layer is made of a material resistible to wearing, e.g., a piece of fabric of synthetic fibers, mixed fabric of natural fibers and synthetic fibers, bonded fabric or paper. Thus, the spreading layer functions as a protective layer. At the same time, the spreading layer has another function of spreading the liquid sample dripped thereon so that the liquid sample is supplied uniformly onto the reagent layer thereunder. The type and material of the reagent layer may be changed according to the target component of the analysis.

Now, the first embodiment of the present invention will be described in detail. In an entire biochemical analyzer, cartridges each containing one or more unused dry chemical analysis elements 1 are housed in a supplier so that transferring means can take a dry chemical analysis element 1 out of a desired cartridge according to the target component of the analysis. Then, a predetermined amount of the liquid sample is dripped on the dry chemical analysis element 1 taken out of the cartridge. This dripping process is carried out by dripping means having a dripping nozzle equipped with a nozzle chip at the tip thereof. The dripping means is moved to a position above a specific container containing a desired liquid sample in liquid sample storing means. Then, the nozzle chip is dipped into the desired liquid sample in the container to absorb the desired liquid sample by a predetermined amount. After the dripping nozzle is moved to a position above a central portion of the dry chemical analysis element 1, the dripping nozzle is moved downward to cause the nozzle chip to drip the liquid sample onto the dry chemical analysis element 1 by a predetermined amount. The dripped liquid sample is spread through the spreading layer and mixes with the reagents contained in the reagent layer. After the liquid sample is dripped, the dry chemical analysis element 1 is inserted into a cell in an incubator so that the dry chemical analysis element 1 is heated up to a predetermined temperature to cause the color reaction (i.e., a pigment-generating reaction) on the reagent layer. Optical density of the pigment generated in the color reaction (i.e., the change in the optical density) is measured by a one-dimensional optical reading apparatus 10 as shown in FIGS. 1 and 2. The change in the optical density is measured after a predetermined time of the color reaction or after each predetermined interval of time.

The one-dimensional optical reading apparatus 10 includes a photometric head 11 for measuring the change in the optical density due to the pigment generated in the color reaction between the reagent layer and the target component contained in the liquid sample. The photometric head 11 projects the measurement light covering a predetermined wavelength guided through a pair of optical fibers 26 and 27 onto the reagent layer from the substrate-side thereof. Output ends of the optical fibers 26 and 27 are located so that a pair of beams of the measurement light are projected onto the reagent layer each with a predetermined angle of incidence. The light reflected by the reagent layer is detected by a photo-detector 14 after going through an optical system.

More specifically, the measurement light to be projected onto the reagent layer is originally generated by a light source (or a lamp) 21 and inputted to input ends of the optical fibers 26 and 27 after going through a lens 22, an interference filter 23 and a lens 25. Then, the measurement light guided to opposite sides of the photometric head 11 via the optical fibers 26 and 27 is projected onto the reagent layer of the dry chemical analysis element 1 through lenses 28. A plurality of the filters 23 have been fitted into windows opened on a circular plate 24, so that an examiner may select any of the filters 23 according to the target component by causing a motor (not shown) to rotate the circular plate 24. The light reflected by the central portion of the reagent layer is collected by a collective lens 12, goes through the aperture 13, and is then detected by the photo-detector 14. The optical density is derived from the light intensity detected by the photo-detector 14.

In measuring the optical density, the dry chemical analysis element 1 is moved in a scanning direction X so that the optical density along a straight line parallel to the scanning direction X is measured. The straight line crosses a central portion of the dry chemical analysis element 1, i.e., a central portion of the reacted portion. In other words, the one-dimensional optical reading apparatus 10 measures the change in optical density along a straight line crossing the central portion of the reacted portion P1 or P2 (see FIGS. 7B and 7C) to obtain one-dimensional distribution of degree of the color reaction, C1 or C2, as shown in FIG. 3A or 3B. Herein, the term "degree of the color reaction" means the same as the term "the change in the optical density." Concurrently, the optical reading apparatus 10 also measures a length L of the reacted portion along the straight line crossing the central portion of the reacted portion, i.e., the width of the distribution C1 or C2.

The physical density or the activity of the target component contained in the liquid sample is determined based on an integrated value Q of the degree of the color reaction and the length L of the reacted portion. Herein, the intensity of the light reflected by the reagent layer carries optical information indicating the amount of the pigment generated within the reagent layer. The reflected light falls onto the photo-detector 14 mounted in the photometric head 11. The optical information is converted in a photometric manner into an electric signal, and the electric signal is transferred to a judging unit through an amplifier.

Figure 7B:
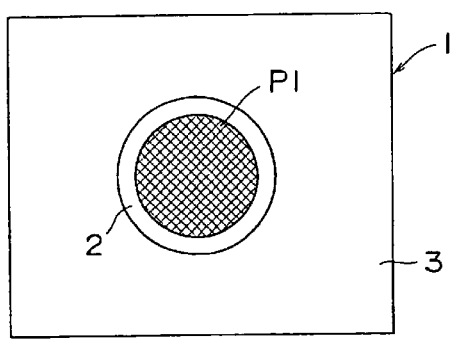
FIGS. 7B and 7C are plane views of the dry chemical analysis element of FIG. 7A, provided with a liquid sample dripped thereon.
Figure 7C:
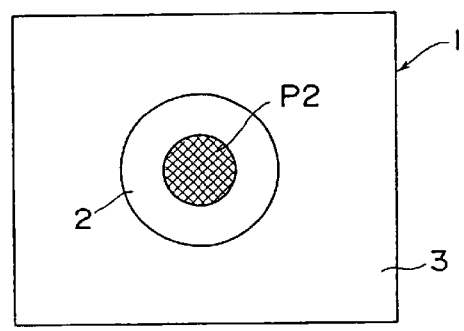
Figure 8:
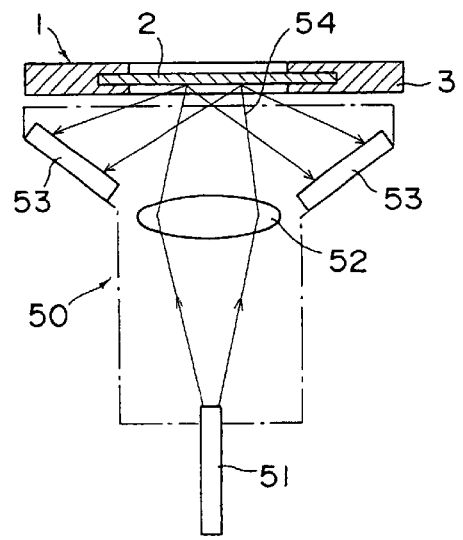
FIG. 8 is a schematic view showing a possible structure of an existing photometric head for measuring the optical density of the reacted portion on the dry chemical analysis element.
Figure 9:
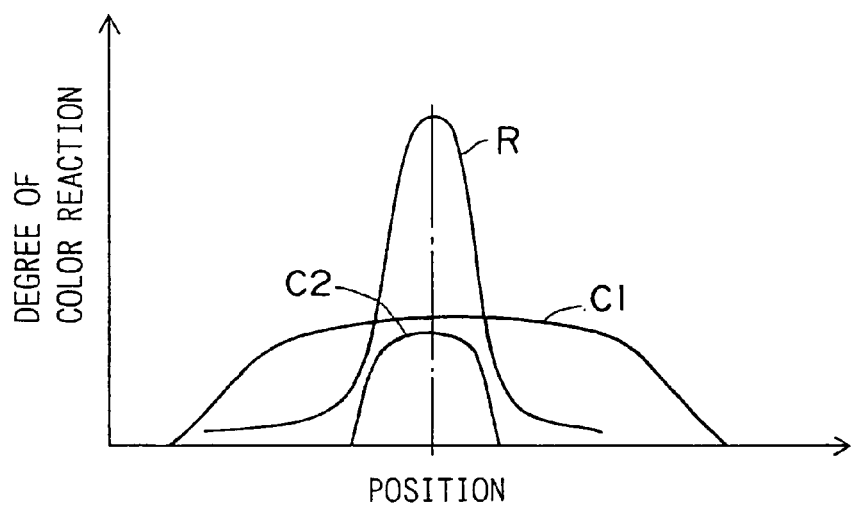
FIG. 9 shows distribution curves in an existing analysis method for the degree of the color reaction and sensitivity of the photometric head.

The distribution C1 of the degree of the color reaction shown in FIG. 3A is an exemplary distribution taken along the straight line crossing the central portion of the reacted portion P1 provided with a sufficient amount of the liquid sample as shown in FIG. 7B. On the other hand, the distribution C2 shown in FIG. 3B is an exemplary distribution taken along the straight line crossing the central portion of the reacted portion P2 provided with an insufficient amount of the liquid sample as shown in FIG. 7C. The integrated value Q of the degree of the color reaction corresponds to the area below the distribution curve C1 or C2 in FIG. 3A or 3B. The length L of the reacted portion corresponds to the width of the distribution curve C1 or C2.

The physical density or the activity of the target biochemical component in the liquid sample is determined based on the integrated value Q of the degree of the color reaction and the length L of the reacted portion, by referring to a predetermined calibration curve showing the relationship between an average degree of the color reaction $D=(Q/L)$ and the physical density or the activity of the target biochemical component. Before referring to the calibration curve, it is desirable to correct the average degree of the color reaction D using a correction coefficient according to spreading characteristics, the length L or the dripped amount of the liquid sample, so that an accurate value of the physical density or the activity can be obtained.

As the one-dimensional optical reading apparatus 10 measures the one-dimensional distribution of the degree of the color reaction along the straight line crossing the central portion of the reacted portion, the accuracy of measurement can be kept sufficiently high even if there is a slight positional difference between the straight line and a line at the exact center of the reacted portion.

Figure 10:
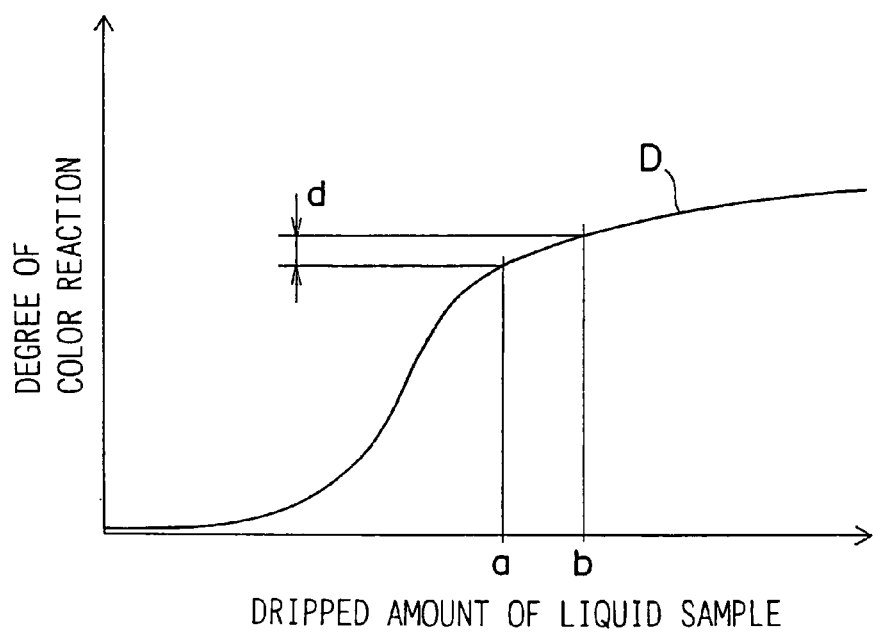
FIG. 10 is a diagram showing the relationship in an existing analysis method between the dripped amount of the liquid sample and the measured degree of the color reaction.

FIG. 5 is a diagram showing a relationship between the dripped amount of the liquid sample and the average degree D of the color reaction. As the dripped amount of the liquid sample increases, the degree of the color reaction at the measured position on the dry chemical analysis element 1 increases because of increase in the liquid sample amount at the measured position. The integrated value Q of the degree of the color reaction and the length L of the reacted portion also increase as the dripped amount increases. However, the average degree of the color reaction, D=(Q/L), becomes almost saturated as shown in FIG. 5, reducing the size of possible error due to fluctuation of the dripped amount of the liquid sample. That is to say, the error d in the average degree of the color reaction due to the fluctuation of the dripped amount of the liquid sample, (b−a), is remarkably lower than the error possibly included in the degree of the color reaction measured by an existing method as shown in FIG. 10. Thus, the examiner may now pay less attention to accurate control of the amount of the liquid sample dripped on the dry chemical analysis element 1.

In the second embodiment of the present invention, the length L of the reacted portion along a straight line crossing the central portion thereof is derived by calculating two boundary positions of the reacted portion based on slopes of the one-dimensional distribution of the degree of the color reaction obtained by the one-dimensional optical reading apparatus 10.

FIG. 4 specifically illustrates the way of deriving the length L of the reacted portion according to the second embodiment. That is, then early-straight portions of the slopes of the distribution curve C3 at both edges are produced until intersecting with the standard line (i.e., the x-axis in FIG. 4) as indicated by broken lines in FIG. 4, so that the distance between two intersections (i.e., two boundary positions) is defined as the length L of the reacted portion. This embodiment is especially effective in the case where the distribution curve C3 obtained by the one-dimensional optical reading apparatus 10 gradually converges to zero at the edges thereof, making the boundary of the spread portion unclear. The physical density or the activity of the target component contained in the liquid sample is thereafter determined based on the integrated value Q of the degree of the color reaction and the length L of the reacted portion in the same manner as the first embodiment.

Figure 6:
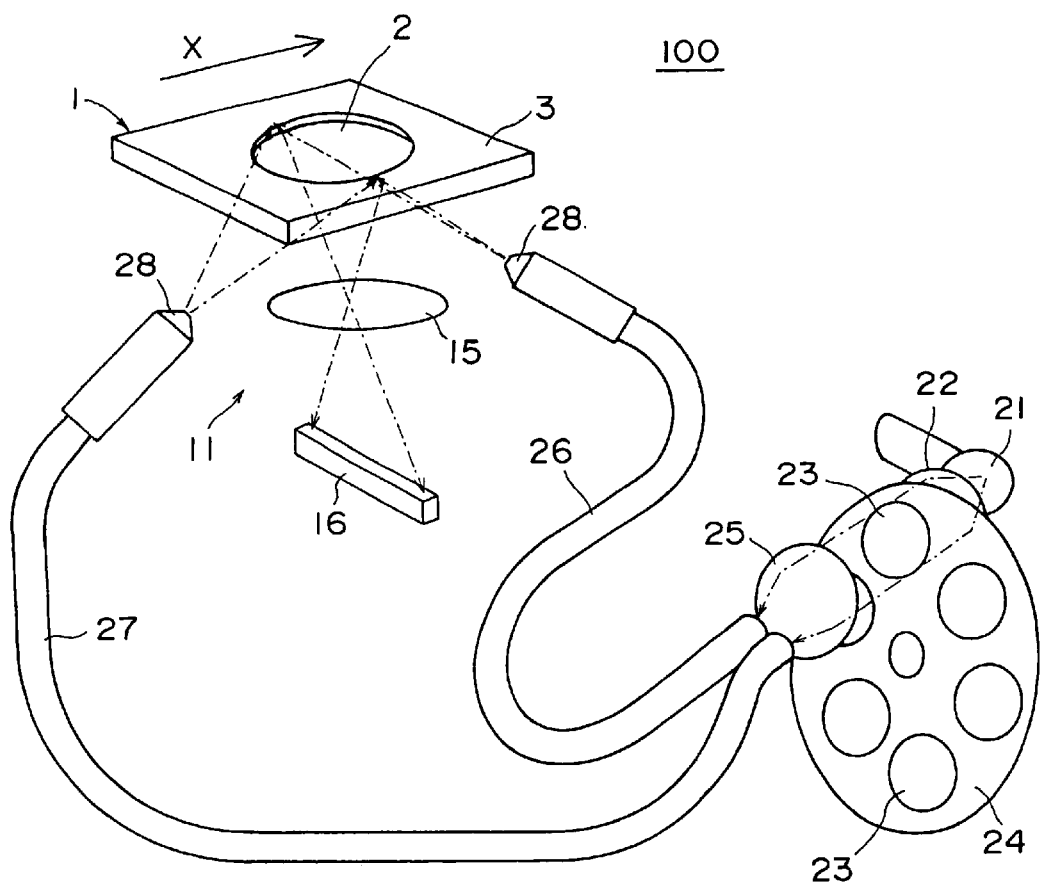
FIG. 6 is a schematic perspective view of a two-dimensional optical reading apparatus used in implementing the third and fourth embodiments of the present invention.

FIG. 6 illustrates a two-dimensional optical reading apparatus 100 for measuring two-dimensional distribution of the degree of the color reaction in analysis methods according to third and fourth embodiments of the present invention.

The two-dimensional optical reading apparatus 100 is substantially the same as the one-dimensional optical reading apparatus 10 shown in FIG. 2 except for the structure of the reflected-light reading portion in the photometric head 11. That is, the measurement light to be projected onto the reagent layer is originally generated by a light source 21 and inputted to input ends of the optical fibers 26 and 27 after going through a lens 22, an interference filter 23 and a lens 25, in the same manner as the above one-dimensional optical reading apparatus 10. The measurement light guided to opposite sides of the photometric head 11 via the optical fibers 26 and 27 is projected onto the reagent layer of the dry chemical analysis element 1 through lenses 28. The reflected light is detected by a line sensor 16 after going through a lens 15. The optical density is derived from the light intensity detected by the line sensor 15.

Now, a third embodiment of the present invention will be described in detail. In measuring the optical density, the dry chemical analysis element 1 is moved in a scanning direction X so that the optical density is measured throughout the surface of the film chip 2. Thus, the two-dimensional optical reading apparatus 100 measures the optical density throughout the reacted portion of the dry chemical analysis element 1 to obtain two-dimensional distribution of the degree of the color reaction. Each one-dimensional section of the obtained two-dimensional distribution will be similar to the curve shown in FIG. 3 (B) The two-dimensional optical reading apparatus 100 concurrently measures length of the reflected light spot using the line sensor 16 for each one-dimensional section of the reacted portion to derive the spread area of the reacted portion therefrom. The physical density or the activity of the target component contained in the liquid sample is thereafter determined by referring to a predetermined calibration curve based on the spread area and the integrated value of the degree of the color reaction.

Also, in the third embodiment, the average degree of the color reaction D as shown in FIG. 5 is derived to reduce possible error due to fluctuation of the dripped amount of the liquid sample. In the case of the third embodiment, Q in FIG. 5 represents the degree of the color reaction integrated over the entire spread area, and the length L of the reacted portion in FIG. 5 is replaced by the spread area S. The average degree of the color reaction D is derived by D=Q/S. Here again, the average degree of the color reaction D becomes almost saturated as shown in FIG. 5, reducing the error d due to fluctuation of the dripped amount of the liquid sample.

In the fourth embodiment of the present invention, the spread area of the reacted portion is derived by producing the nearly-straight portions of the slopes of the distribution curve obtained by the two-dimensional optical reading apparatus 100 until the produced lines intersect with the standard line, in the similar manner as the second embodiment described in reference to FIG. 4, so that the boundary of the reacted portion is defined appropriately.

Although a line sensor 16 is used as a photo-detector for the two-dimensional optical reading apparatus 100 in the third and fourth embodiments, it may be replaced by an array detector. In that case, the two-dimensional distribution of the degree of the color reaction can be obtained without moving the dry chemical analysis element 1 in the scanning direction X.

Although the dry chemical analysis element 1 used in the above embodiments is a slide-type element including the frame 3, any other suitable type of the dry chemical element may instead be used. For example, a slide-type element without a frame or a filter-paper type element can be used.

What is claimed is:

1. An analysis method using a dry chemical analysis element, wherein the method comprises:
   dripping a liquid sample onto the dry chemical analysis element comprising a reagent layer;
   measuring a change in optical density of a reacted portion on the dry chemical analysis element where color reaction between the liquid sample and the reagent layer has occurred; and
   determining physical density or activity of a specific biochemical component contained in the liquid sample;
   wherein measuring the change in the optical density comprises:
   measuring one-dimensional distribution of the change in the optical density along a straight line crossing a central portion of the reacted portion by causing a one-dimensional optical reading apparatus to scan the straight line; and
   measuring a length of the reacted portion along the straight line crossing the central portion of the reacted portion using the one-dimensional optical reading apparatus; and wherein the physical density or the activity is determined based on an integrated value of the change in the optical density and the measured length of the reacted portion.

2. An analysis method using a dry chemical analysis element, wherein the method comprises:

dripping a liquid sample onto the dry chemical analysis element comprising a reagent layer;

measuring a change in optical density of a reacted portion on the dry chemical analysis element where color reaction between the liquid sample and the reagent layer has occurred; and determining physical density or activity of a specific biochemical component contained in the liquid sample; wherein measuring the change in the optical density comprises:

measuring one-dimensional distribution of the change in the optical density along a straight line crossing a central portion of the reacted portion by causing a one-dimensional optical reading apparatus to scan the straight line;

calculating two boundary positions of the reacted portion based on slopes of the obtained one-dimensional distribution of the change in the optical density; and defining a distance between the two boundary positions as a length of the reacted portion; and wherein the physical density or the activity is determined based on an integrated value of the change in the optical density and the defined length of the reacted portion.

3. An analysis method using a dry chemical analysis element, wherein the method comprises:

dripping a liquid sample onto the dry chemical analysis element comprising a reagent layer;

measuring a change in optical density of a reacted portion on the dry chemical analysis element where color reaction between the liquid sample and the reagent layer has occurred; and determining physical density or activity of a specific biochemical component contained in the liquid sample; wherein measuring the change in the optical density comprises:

measuring two-dimensional distribution of the change in the optical density over an entire spread area of the reacted portion by causing a two-dimensional optical reading apparatus to scan the entire spread area; and measuring the spread area of the reacted portion using the two-dimensional optical reading apparatus; and wherein the physical density or the activity is determined based on an integrated value of the change in the optical density and the measured spread area.

4. An analysis method using a dry chemical analysis element, wherein the method comprises:

dripping a liquid sample onto the dry chemical analysis element comprising a reagent layer;

measuring change in optical density of a reacted portion on the dry chemical analysis element where color reaction between the liquid sample and the reagent layer has occurred; and determining physical density or activity of a specific biochemical component contained in the liquid sample; wherein measuring the change in the optical density comprises:

measuring two-dimensional distribution of the change in the optical density over an entire spread area of the reacted portion by causing a two-dimensional optical reading apparatus to scan the entire spread area;

calculating a boundary of the reacted portion based on slopes of the measured two-dimensional distribution of the change in the optical density; and defining an area within the calculated boundary as the spread area of the reacted portion; and wherein the physical density or the activity is determined based on an integrated value of the change in the optical density and the measured spread area of the reacted portion.

* * * * *